United States Patent [19]

Fleck et al.

[11] 4,167,626
[45] Sep. 11, 1979

[54] TRIAZOLYL STILBENE TRIAZOLES

[75] Inventors: Fritz Fleck, Bottmingen, Switzerland; Alec V. Mercer, Leeds; Roger Paver, Bingley, both of England

[73] Assignee: Sandoz Ltd., Basel, Switzerland

[21] Appl. No.: 818,007

[22] Filed: Jul. 22, 1977

Related U.S. Application Data

[63] Continuation of Ser. No. 603,252, Aug. 11, 1975, abandoned.

[51] Int. Cl.² .......................................... C07D 403/14
[52] U.S. Cl. ............................. 542/435; 252/301.22; 252/301.29; 162/162; 548/255
[58] Field of Search ..................... 542/435; 60/3, 252

[56] References Cited

U.S. PATENT DOCUMENTS 3,928,329  12/1975  Fleck et al. ........................ 542/435

FOREIGN PATENT DOCUMENTS 1320836  7/1970  United Kingdom.

Primary Examiner—Arthur P. Demers
Attorney, Agent, or Firm—Gerald D. Sharkin; Richard E. Vila; Thomas C. Doyle

[57] ABSTRACT

Disclosed are compounds of formula I,

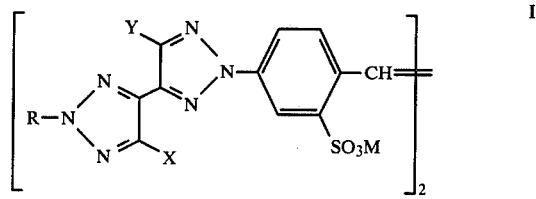

in which X signifies hydrogen, $C_{1-4}$alkyl, cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, Y signifies hydrogen, $C_{1-4}$alkyl, cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, with the proviso that X and Y do not simultaneously have a significance selected from hydrogen and $C_{1-4}$alkyl, R signifies an aryl radical, unsubstituted or substituted by up to two substituents selected from $C_{1-4}$ alkyl, $C_{1-4}$ alkoxy, chlorine, cyano, —COOM, —COOR$_1$, —CONR$_4$R$_5$, —SO$_2$NR$_4$R$_5$, —SO$_2$R$_1$ and —SO$_3$M, R$_1$ signifies $C_{1-4}$alkyl or phenyl, R$_2$ and R$_3$, independently, signify hydrogen or $C_{1-4}$alkyl, either R$_4$ and R$_5$, independently, signify hydrogen or $C_{1-4}$alkyl, or R$_4$ and R$_5$, together with the nitrogen atom to which they are attached, signify a five or six membered heterocyclic radical, and the M's, independently, signify hydrogen or a non-chromophoric cation, their production and use as anionic optical brightening agents, particularly for cellulosic and polyamide substrates.

11 Claims, No Drawings

TRIAZOLYL STILBENE TRIAZOLES

This is a continuation of application Ser. No. 603,252, filed Aug. 11, 1975, now abandoned.

The invention relates to triazolyl stilbenyl triazoles.

The invention provides compounds of formula I,

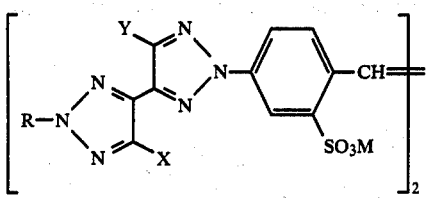

in which X signifies hydrogen, $C_{1-4}$alkyl, cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, Y signifies hydrogen, $C_{1-4}$alkyl, cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, with the proviso that X and Y do not simultaneously have a significance selected from hydrogen and $C_{1-4}$alkyl, R signifies an aryl radical, preferably a naphthyl or phenyl radical, more preferably a phenyl radical, which aryl radical is unsubstituted or substituted by up to two substituents, preferably one substituent, selected from $C_{1-4}$alkyl, $C_{1-4}$alkoxy, chlorine, cyano, —COOM, —COOR$_1$, —CONR$_4$R$_5$, —SO$_2$NR$_4$R$_5$, —SO$_2$R$_1$ and —SO$_3$M, R$_1$ signifies $C_{1-4}$alkyl or phenyl, R$_2$ and R$_3$, independently, signify hydrogen or $C_{1-4}$-alkyl, either R$_4$ and R$_5$, independently, signify hydrogen or $C_{1-4}$alkyl, or R$_4$ and R$_5$, together with the nitrogen atom to which they are attached, signify a five or six membered heterocyclic radical, preferably a piperidine or morpholino radical, and the M's, independently, signify hydrogen or a non-chromophoric cation.

In the compounds of formula I, X preferably signifies hydrogen or $C_{1-4}$alkyl, more preferably $C_{1-4}$-alkyl and most preferably methyl.

Y preferably signifies cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, more preferably cyano, —COOM, methoxycarbonyl, ethoxycarbonyl, —CONH$_2$, —SO$_2$CH$_3$ or —SO$_3$M, particularly —CONH$_2$, ethoxycarbonyl, —COOM or —SO$_3$M.

As indicated above, R preferably signifies a phenyl or naphthyl radical unsubstituted or substituted by two or preferably one substituent selected from the list hereabove given. Any disubstituted phenyl or naphthyl as R preferably bears other than two cyano groups and, indeed, any disubstituted phenyl or naphthyl preferably bears, as one of the substituents, an —SO$_3$M group. The preferred di-substituted phenyls as R bear one —SO$_3$M group and methyl, $C_{1-2}$alkoxy or chlorine. Thus, R preferably signifies phenyl, unsubstituted, mono-substituted by a substituent selected from methyl, $C_{1-2}$alkoxy, chlorine, cyano, —CONH$_2$, —COOM, $C_{1-2}$alkoxycarbonyl, —SO$_2$CH$_3$, —SO$_2$NH$_2$ and —SO$_3$M, or disubstituted, once by —SO$_3$M and once by methyl, $C_{1-2}$alkoxy or chlorine. Most preferably R signifies unsubstituted phenyl or phenyl mono-substituted by cyano, methoxy, chlorine or —SO$_3$M.

Where M signifies a cation, the exact nature thereof is not critical provided it is non-chromophoric. Cations conventional in the optical brightening art, to which the present invention relates, may be employed. As examples of suitable cations may be given the alkali-metal cations, e.g. of sodium, potassium or lithium, the alkaline earth metal cations and the ammonium, alkylammonium and alkanolammonium cations, e.g. of formula R$_9$R$_{10}$R$_{11}$N⊕H, where R$_9$, R$_{10}$ and R$_{11}$, independently, signify hydrogen or $C_{1-4}$-alkyl, unsubstituted or substituted by one or two, preferably one, hydroxy group, e.g. the mono-, di- and triethanolammonium and mono-, di and tri-isopropanol-ammonium cations. Any hydroxy group in any alkanolammonium cation is preferably at least two carbon atoms removed from the nitrogen. The preferred cations are the alkali-metal cations, particularly of sodium or potassium, and more particularly of the former.

As representative of compounds of formula I, may be given the compounds of formula I',

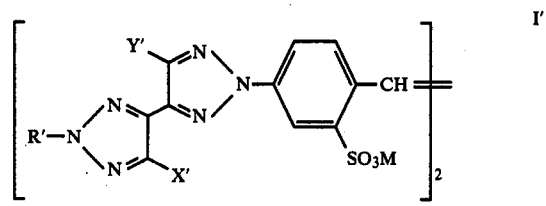

in which X' signifies hydrogen or $C_{1-4}$alkyl, preferably $C_{1-4}$alkyl, more preferably methyl, Y' signifies cyano, —COOM, —COOR$_1$, —CONR$_2$R$_3$, —SO$_2$NR$_2$R$_3$, —SO$_2$R$_1$, —SOR$_1$, —SO$_3$R$_1$ or —SO$_3$M, R' signifies a phenyl or naphthyl radical (preferably a phenyl radical), which radical is unsubstituted or substituted by up to two substituents, preferably one substituent, selected from $C_{1-4}$alkyl, $C_{1-4}$-alkoxy, chloro, cyano, —COOM, —COOR$_1$, —CONR$_4$R$_5$, —SO$_2$NR$_4$R$_5$, —SO$_2$R$_1$ and —SO$_3$M, R$_1$, R$_2$, R$_3$, R$_4$ and R$_5$ and the M's being as defined above.

As representative of the compounds of formula I' may be given the compounds of formula I'',

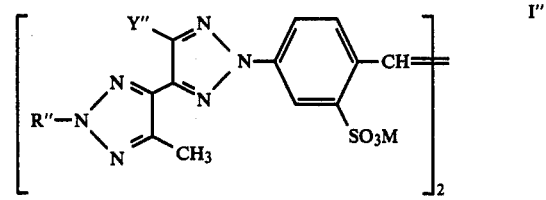

in which Y'' signifies —COOM, —COOR$_1$'', —CONH$_2$, or —SO$_3$M,

R'' signifies phenyl, unsubstituted or mono- or di-substituted by methyl, $C_{1-2}$alkoxy, chlorine, cyano, —CONH$_2$, —COOM, —COOR$_1$'', —SO$_2$CH$_3$, —SO$_2$NH$_2$ or —SO$_3$M, R$_1$'' signifies $C_{1-2}$alkyl, and the M's are as defined above.

In the compounds of formula I' and I", the preferred mono- and disubstituted phenyl radicals as R' and R" are those given above for R.

In the compounds of formula I, X and Y are preferably other than —SOR$_1$, as is Y' in compounds I'.

In the compounds of formula I", when Y" is —COOM, —COOR$_1$" or —CONH$_2$, R" is preferably unsubstituted phenyl or phenyl mono-substituted by methyl, methoxy, chlorine or —SO$_3$M, such substituent preferably being in the 3- or 4-position of the phenyl ring. When Y" is —SO$_3$M, R" is preferably phenyl mono-substituted by —SO$_3$M or phenyl disubstituted, once by —SO$_3$M and once by methyl, methoxy or chlorine, the methyl, methoxy or chlorine preferably being in the 3- or 4-position of the phenyl ring.

The invention also provides a process for the production of compounds of formula I, characterised by (a) producing a compound of formula I by cyclising a keto- or imino-hydrazone of formula II,

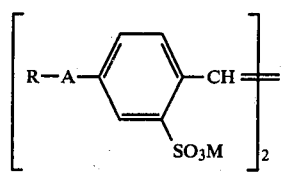

in which R and M are as defined above, and
—A— signifies (a), (b) or (c),

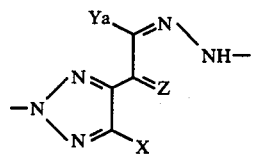

in which X is as defined above, preferably hydrogen or C$_{1-4}$alkyl,
Z signifies —O— or —NH,
Ya has the same significance as Y, above, with the proviso that it is other than hydrogen, C$_{1-4}$alkyl or —COOH,

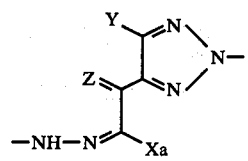

in which Y and Z are as defined above, Y preferably signifying hydrogen or C$_{1-4}$-alkyl, and
Xa has the same significance as X, above, with the proviso that it is other than hydrogen, C$_{1-4}$alkyl or —COOH,

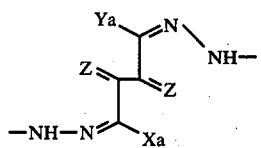

in which Z is as defined above, and in which Ya and Xa are as defined above, but preferably have the same significance, and, where required, where in the resulting compound X or Y is —COOM', where M' is a non-chromophoric cation, converting such into a compound where X or Y is —COOH by treatment with acid, (b) obtaining a compound of formula I, in which X signifies hydrogen, C$_{1-4}$alkyl, —SO$_2$R$_1$, —SOR$_1$, —SO$_2$NR$_2$R$_3$, or —SO$_3$M, preferably hydrogen or C$_{1-4}$alkyl, and Y signifies —SO$_2$R$_1$, —SOR$_1$, —SO$_2$NR$_2$R$_3$ or —SO$_3$M, by cyclisation of a compound of formula III,

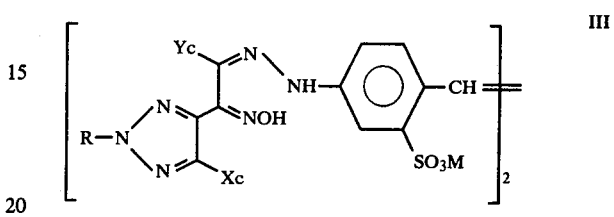

in which Xc signifies hydrogen, C$_{1-4}$alkyl, —SO$_2$R$_1$, —SOR$_1$, —SO$_2$NR$_2$R$_3$ or —SO$_3$M, preferably hydrogen or C$_{1-4}$alkyl,
Yc signifies —SO$_2$R$_1$, —SOR$_1$, —SO$_2$NR$_2$R$_3$ or —SO$_3$M, (c) obtaining a compound of formula I, in which X has a significance of Xc, above, and Y signifies —SO$_2$R$_1$, —SOR$_1$, —SO$_2$NR$_2$R$_3$, —CN, —COOR$_1$, —CONR$_2$R$_3$ or —SO$_3$M, by cyclisation of a compound of formula IV,

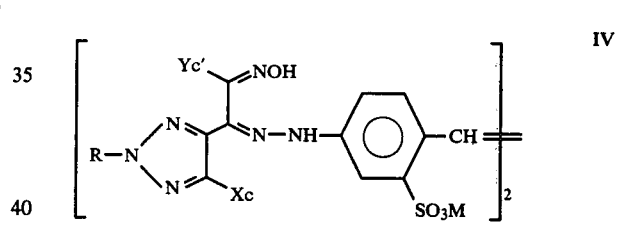

in which Xc is as defined above, and
Yc' signifies —SO$_2$R$_1$, —SOR$_1$, —SO$_2$NR$_2$R$_3$, —CN, —COOR$_1$, —CONR$_2$R$_3$ or —SO$_3$M, (d) obtaining a compound of formula I, in which X has a significance of Yc, above, and Y signifies H, C$_{1-4}$alkyl, —SO$_2$R$_1$, —SOR$_1$, —SO$_2$NR$_2$R$_3$, or —SO$_3$M, preferably hydrogen or C$_{1-4}$alkyl, by cyclisation of a compound of formula V,

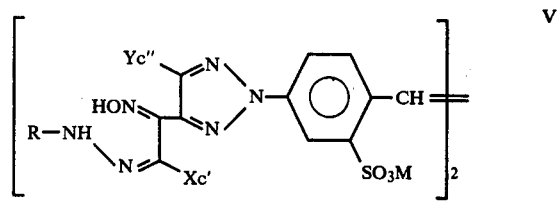

in which Xc' has a significance of Yc, above, and
Yc" signifies hydrogen, C$_{1-4}$alkyl, —SO$_2$R$_1$, —SOR$_1$, —SO$_2$NR$_2$R$_3$, or —SO$_3$M, preferably hydrogen or C$_{1-4}$alkyl, (e) obtaining a compound of formula I, in which Y has a significance of YC", above, and X has a significance of Yc', above, by cyclisation of a compound of formula VI,

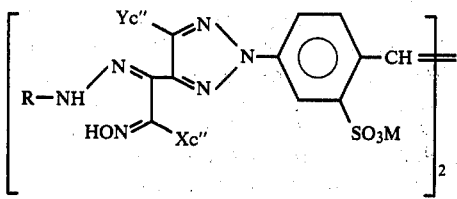

in which Yc″ is as defined above, and
Xc″ has a significance of YC′, above, (f) obtaining a compound of formula I, in which X and Y each have a significance of Yc, above, preferably both having the same significance, by (i) cyclisation of a compound of formula VII,

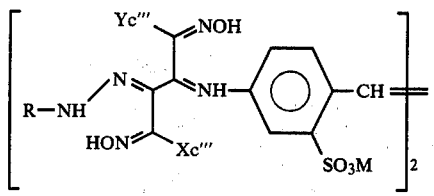

in which Yc‴ and Xc‴ each have a significance of Yc, above, preferably both having the same significance, or by (ii) cyclising a compound of formula VIII,

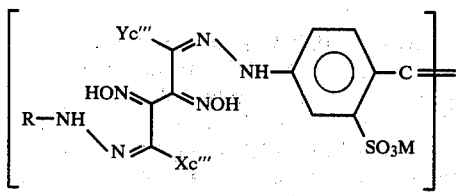

in which Yc‴ and Xc‴ are as defined above, (g) obtaining the compound of formula I obtained, respectively, in each of the above processess (b) to f(ii) by reducing the N-oxides obtained by oxidative cyclisation of compounds III, IV, V, VI, VII and VIII, respectively.

The above processes may be carried out in manner conventional for the types of reaction involved.

Thus, in process (a), the cyclisation is suitably carried out using a cupric salt, such as cupric chloride, cupric bromide, cupric sulphate or cupric acetate, in the presence of excess ammonia, e.g. as concentrated aqueous ammonia or a stream of ammonia, when Z signifies NH, or in the presence of an ammonium salt of an organic acid, e.g. ammonium acetate, formate or propionate, when Z signifies O. In the reaction, an excess of the cupric salt would normally be used but, if desired, the reaction can be carried out in the presence of catalytic amounts thereof if a stream of air or oxygen is passed through the reaction medium. The reaction is carried out in a solvent, suitably in water or in a mixture of water and an organic solvent, such as in aqueous methanol, pyridine, ethanol, 2-ethoxyethanol or dimethyl formamide. A suitable reaction temperature is from 20° to 200° C., preferably from 70° to 130° C. A suitable reaction time is from 0.5 to 100 hours, usually from 2 to 48 hours.

In processes (b) to f(ii), the cyclisation is conveniently carried out by treating the oximino hydrazone compounds III to VIII with a dehydrating agent. As examples of dehydrating agents may be given anhydrides of organic acids, e.g. acetic and propionic anhydride, preferably in the presence of a salt of an organic acid, e.g. sodium or potassium acetate, phosphorus halides, e.g. phosphorus trichloride, phosphorus oxyhalides, e.g. phosphorus oxychloride, organic isocyanates or phosgene. The reaction is suitably carried out in an inert solvent, such as in dimethylformamide or pyridine, or, where an organic acid anhydride is used as dehydrating agent, in an excess thereof, the excess serving as solvent. A suitable reaction temperature is from 0° to 200° C., preferably from 30° to 130° C. The reaction time may be from 0.5 to 200 hours but generally is from 2 to 6 hours. Alternatively, the oximinohydrazone compounds III to VIII can be cyclised by heating in urea at a temperature of from 90° to 210° C., preferably from 130° to 180° C., optionally in the presence of an inert solvent such a as ethylene glycol, diethylene glycol or sulpholane, but preferably using more than one equivalent of urea in the absence of an additional solvent.

Still further, the cyclisation may be carried out according to the method described in D.O.S. No. 2,242,784.

In the process (g), reduction of the triazole N-oxides is conveniently carried out using such reducing agents as zinc dust/acetic acid and iron/acetic acid.

The N-oxides, employed as starting materials in process (h), may be obtained by oxidative cyclisation of compounds III to VIII in conventional manner. Such cyclisation is conveniently carried out in an inert solvent, such as in water and/or an organic solvent. Suitable organic solvents include dimethylformamide, phosphoric acid trisdimethylamide, sulphones, such as tetramethylene sulphone or organic bases such as pyridine. As examples of oxidising agents may be given sodium bichromate, hydrogen peroxide and cupric salts, e.g. cupric sulphate. A suitable reaction temperature is from 20° to 130° C., preferably from 60° to 110° C. The reaction time may be from 0.5 to 24 hours, usually from 1 to 6 hours.

Compounds of formula I, obtained by the above processes may, as will be appreciated, be inter-converted to other compounds of formula I. For example, any cyano group may be converted into a —$CONH_2$ group, e.g. by treatment with polyphosphoric acid or alkaline hydrogen peroxide. Any —$COOR_1$ group may be hydrolysed to the free acid and, if desired, isolated in salt form, or such group may be converted to a —$CONR_2R_3$ group by treatment with appropriate amines. Any —COOM group may be converted into a —$CONH_2$ group by first converting to the acid chloride, e.g. by treatment with thionyl chloride, followed by treatment with ammonia. Any —$CONH_2$ group may be converted to a cyano group, e.g. by treatment with phosphorus oxychloride and any —COOM group may be esterified to yield the —$COOR_1$ group. Also, compounds in which R is sulphophenyl may be obtained by sulphonation of compounds where R is phenyl. Such inter-conversions may be carried out in conventional manner for the types of reaction involved.

The resulting compounds of formula I may be isolated and purified in conventional manner.

The compounds of formulae II to VIII may be obtained in conventional manner from available starting materials.

The compounds of formula I are indicated for use as optical brightening agents for substrates brightenable using anionic brightening agents, particularly for polyamide substrates and most particularly for nylon substrates. Such substrates may be of a textile or nontextile nature. Where textile in nature, such substrates may be in fibre, yarn, woven, non-woven, knitted or other desired form.

The compounds of formula I are particularly suitable for application to polyamide substrates from an acid exhaust bath containing or free from sodium chlorite. Such application may be carried out in conventional manner using conventional amounts of brightener and liquor to goods ratios. For example, the compounds of formula I may be applied to the substrate in an amount of from 0.01 to 1%, preferably from 0.05 to 0.5% based on the weight of the substrate, the application being conveniently at a liquor to goods ratio of from 10:1 to 100:1.

The compounds of formula I are also indicated for use in the brightening of cellulosic substrates, particularly cotton and more particularly resin finished cotton for which use the compounds may be added to the synthetic resin in the treatment liquor or applied to the substrate prior to application of the resin. Advantageously, 0.02 to 1.2%, preferably 0.05 to 0.8% of brightener relative to the substrate is employed in this case. Particularly good results are obtained by this method when cross-linking of the resin is catalysed using zinc nitrate.

The following Examples, in which all parts and percentages are by weight, unless otherwise stated, and all temperatures in degrees centigrade, illustrate the invention.

EXAMPLE 1

4,4'-diamino stilbene-2,2'-disulphonic (18.5 g) was dissolved in water (100 ml) and sodium carbonate (5.4 g). Concentrated hydrochloric acid S.G.1.18 (25 ml) was added and the mixture cooled to 5°–10°. Sodium nitrite (7 g) was then added during 1 hour at 5° to 10°. The tetrazonium suspension was then added during 30 minutes to a suspension of 2-phenyl-4-methyl-5-sulphoacetyl-γ-triazole (sodium salt) (32 g) in a mixture of water (250 ml) and ethyl alcohol (50 ml). The pH was maintained at 5 by the addition of sodium acetate (10 g). Pyridine (25 ml) was added and the mixture stirred 1 hour at 20°–30°, and then 1 hour at 40°, and finally 30 minutes at 50°. Sodium chloride (50 g) was added, and the red coloured suspension of ketohydrazone cooled to 5°, filtered and washed with 150 ml 10% W/V sodium chloride solution and dried.

The dry keto hydrazone (62.6 g) was stirred in a mixture of water (90 ml), cellosolve (150 ml) and cupric chloride dihydrate (36.36 g), and ammonium acetate (80 g) then added. The mixture was refluxed 16 hours, cooled to 80° and sodium sulphide dihydrate (28 g) added carefully. The precipitated copper sulphide was filtered and the filtrates cooled to 10°. The precipitated yellow product was filtered, washed with 10% W/V sodium chloride solution (300 ml) and then recrystallised from a mixture of water and ethyl alcohol to give the triazole of formula

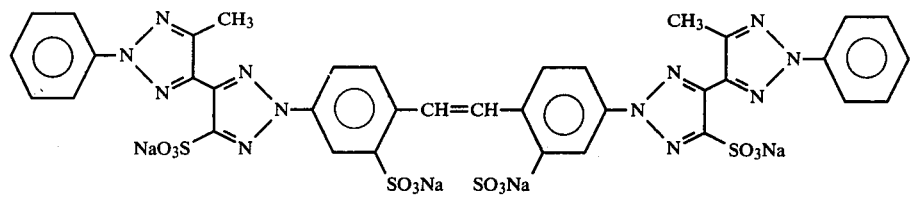

The 2-phenyl-4-methyl-5-sulphoacetyl-ν-triazole (sodium salt) was prepared by the following procedure:

2-phenyl-4-methyl-5-acetyl-ν-triazole (40.2 g) was dissolved in glacial acetic acid (140 ml) at 20°–25°. Bromine (10.8 ml) was then added during 1 hour at 20°–25°. The mixture was stirred 1 hour at 20°, cooled to 10° and the crystalline product filtered and washed with 1:1 ethanol: water (250 ml). The solid was dried at 50° to give 2-phenyl-4-methyl-5-bromoacetyl-ν-triazole as an off white coloured solid m.p. 74°–76°.

2-phenyl-4-methyl-5-bromoacetal-ν-triazole (56 g) was added to ethyl alcohol (90 ml) and warmed to 50°. A solution of anhydrous sodium sulphite (35 g) in water (140 ml) was added and the mixture heated at reflux for 30 minutes. The solution was cooled to 5°, filtered and the white coloured crude product washed with water (50 ml). The crude product was recrystallised from water/ethanol (1:1) (200 ml) to give 2-phenyl-4-methyl-5-sulphoacetyl-ν-triazole (sodium salt) as a white crystalline compound of formula

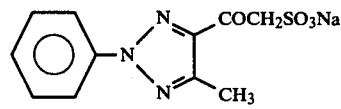

2-phenyl-4-methyl-5-acetyl-ν-triazole was prepared by the method described in Swiss Pat. No. 444,873.

EXAMPLE 2

Following the procedure described in Example 1, but replacing the 32 g of 2-phenyl-4-methyl-5-sulphoacetyl-ν-triazole (sodium salt) with 34.6 g of 2-p-cyanophenyl-4-methyl-5-sulphoacetyl-ν-triazole one obtains (after recrystallisation from 50% aqueous dimethylformamide) a pale yellow coloured triazole of formula

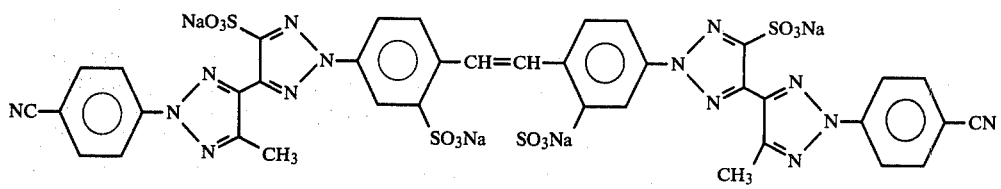

2-p-cyanophenyl-4-methyl-5-sulphoacetyl-ν-triazole (sodium salt) was obtained by the following procedure.

2-p-cyanophenyl-4-methyl-5-acetyl-ν-triazole (27.7 g) was dissolved in glacial acetic acid (192 ml) at 60° C. Bromine (7.45 ml) was added at 60° over 1 hour. The reaction was then stirred for a further 1 hour at 60°. The mixture was cooled to 5° and the off-white coloured product filtered and washed with 1:1 ethanol: water. The solid was dried at 60° to give 32.7 g of 2-p-cyanophenyl-4-methyl-5-bromo acetyl-ν-triazole m.p. 146°.

2-p-cyanophenyl-4-methyl-5-bromoacetyl-ν-triazole (32.6 g) was added to ethyl alcohol (97 ml) and warmed to 50° C. A solution of anhydrous sodium sulphite (20.4 g) in water (82 ml) was added and the mixture heated at reflux for 30 minutes. The solution was cooled to 5° and the white precipitate filtered and washed with 2% W/V sodium chloride solution (20 ml). The product was dried at 60° to give 2-p-cyanophenyl-4-methyl-5-sulphoacetyl-ν-triazole (sodium salt) as a white solid of formula

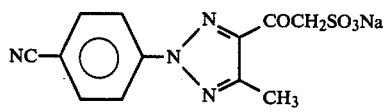

2-p-cyanophenyl-4-methyl-5-acetyl-ν-triazole m.p. 137°–139° was prepared by cyclisation of the imino hydrazone of formula

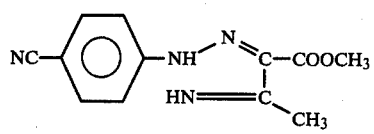

by a method similar to that described in Swiss Pat. No. 444,873 for the preparation of 2-phenyl-4-methyl-5-acety-ν-triazole.

EXAMPLE 2a

By treatment of the compound produced in Example 2 with alkaline hydrogen peroxide there may be produced the compound of formula

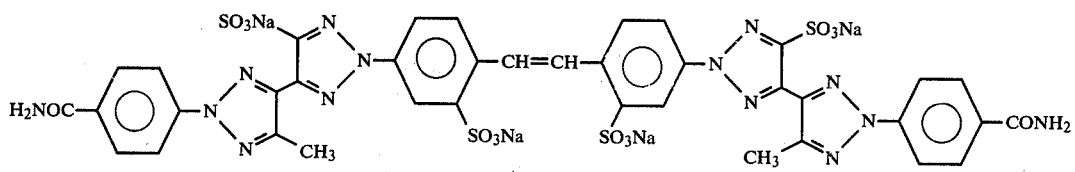

as a yellow powder.

EXAMPLE 3

Following the procedure described in Example 1 but replacing the 32 g of 2-phenyl-4-methyl-5-sulphoacetyl-ν-triazole (sodium salt) with 36.3 g of 2-p-methoxyphenyl-4-methyl-5-sulphoacetyl-ν-triazole (sodium salt) one obtains (after recrystallisation from ethanol: water (1:1)) a pale yellow coloured triazole of formula

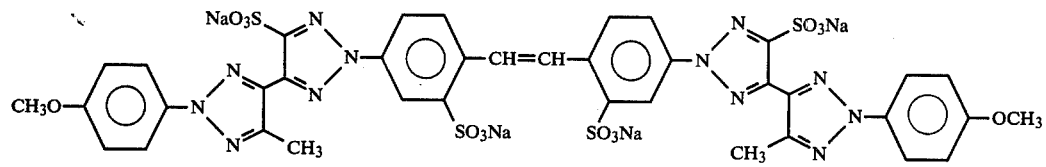

2-p-methoxyphenyl-4-methyl-5-sulphoacetyl-ν-triazole (sodium salt) was obtained by the following procedure:

2-p-methoxyphenyl-4-methyl-5-acetyl-ν-triazole (69.3 g) was dissolved in glacial acetic acid (285 ml) at 40°. Bromine (16.2 ml) was added over 30 minutes and the mixture maintained at 40°–60° for 2 hours, cooled to 10° and ethyl alcohol (30 ml) added. The white coloured suspension was stirred 30 minutes at 10°, filtered, and the white coloured solid washed with 50% aqueous ethyl alcohol (400 ml). The product was dried at 60° to give 68.23 g of 2-p-methoxy-phenyl-4-methyl-5-bromoacetyl-ν-triazole.

2-p-methoxyphenyl-4-methyl-5-bromoacetyl-ν-triazole (68 g) was slurried in ethyl alcohol (79 ml) at 50°. A solution of anhydrous sodium sulphite (46.9 g) in water (234 ml) was added and the mixture refluxed for 1 hour. The solution was then cooled to 5° and the crystalline suspension filtered and washed with 5% W/V sodium chloride solution. The white coloured product was recrystallised from 50% aqueous ethyl alcohol and the white coloured product dried at 60° to give 55.21 g of 2-p-methoxy-phenyl-4-methyl-5-sulphoacetyl-ν-triazole (sodium salt) formula:

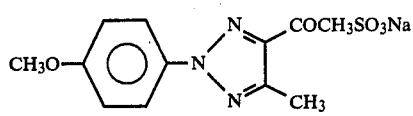

2-p-methoxyphenyl-4-methyl-5-acetyl-v-triazole m.p. 95°–97° was synthesised by cyclisation of the imino hydrazone of formula

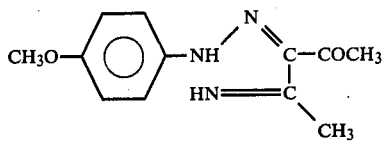

by a method similar to that described in Swiss Pat. No. 444,873 (Isis-Chemis KG) for the preparation of 2-phenyl-4-methyl-5-acetal-v-triazole.

Following the procedure of Example 3, above, using appropriate starting materials, the compounds in the following table are obtained and which are of formula

EXAMPLE 4

4:4'-diaminostilbene-2:2'-disulphonic acid (18.5 g) was tetrazotised by the procedure described in Example 1 and the resulting tetrazonium suspension added during 30 minutes to 2-phenyl-4-methyl-5-carbethoxy acetyl-v-triazole (27.8 g) in ethyl alcohol (400 ml) at 10°–15°, pH being kept at 5–6 by addition of anhydrous sodium acetate (10 g). Pyridine (30 ml) was added and the mixture heated over 2 hours to 50°. The orange-red coloured suspension of keto-hydrazone was cooled to 10°, filtered and washed with water (200 ml).

The keto hydrazone was added to cellosolve (500 ml) and water (250 ml), and ammonium acetate (78.6 g) and cupric chloride dihydrate (36.36 g) then added. The mixture was refluxed 18 hours, sodium chloride (60 g) added and the mixture cooled to 20° filtered and the yellow coloured solid washed with water (400 ml). The yellow coloured solid was dissolved in a mixture of cellosolve (300 ml) and water (100 ml) W/W sodium hydroxide solution (50 ml) added. The mixture was refluxed for 90 minutes and 2 g sodium hydrosulphite and sodium chloride (60 g) added. The pale yellow precipitate was cooled to 5°, filtered and washed with 10% W/W sodium chloride solution (100 ml). The pale yellow solid was recrystallised from water (70 ml), isopropanol (20 ml) to give the triazole of formula:

| Example No. | R | Appearance |
|---|---|---|
| 3a | $NaO_2C-C_6H_4-$ | yellow solid |
| 3b | $H_3CO_2C-C_6H_4-$ | " |
| 3c | $H_3CO_2S-C_6H_4-$ | " |
| 3d | $H_2NO_2S-C_6H_4-$ | " |
| 3e | $3-CH_3-C_6H_4-$ | " |
| 3f | $CH_3-C_6H_4-$ | " |
| 3g | $Cl-C_6H_4-$ | " |

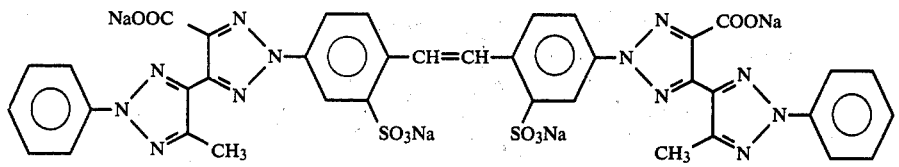

2-phenyl-4-methyl-5-carbethoxy acetyl-v-triazole was prepared by the following procedure:

Sodium metal (6.93 g) was added to dry toluene (350 ml) and heated to 90°, absolute ethyl alcohol (75 ml) was added and the mixture refluxed until all the sodium had dissolved. The unreacted ethyl alcohol was then distilled out of the mixture and a solution of 2-phenyl-4-methyl-5-carbethoxy-v-triazole (46.2 g) in ethyl acetate (42.7 ml) was added. The mixture was refluxed for 3 hours, cooled to 30°, filtered and the fawn coloured solid washed with ether (100 ml). The solid was added to a mixture of water (250 ml) and acetic acid (250 ml) and the concentrated hydrochloric acid (50 ml) added. The mixture was extracted with 3×300 ml of diethyl ether and the ether layer washed with 10% sodium carbonate (300 ml) and then with water (500 ml). The ether extract was dried over anhydrous sodium sulphate and then evaporated to leave a pale brown coloured oil. The oil was distilled to give 28.5 g of 2-phenyl-4-methyl-5-carbethoxy acetyl-v-triazole as a pale yellow solid (m.p. 43°-45° b.p. 191° at 0.9 m.m.Hg) of formula

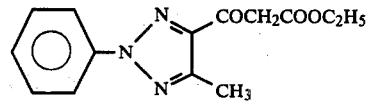

2-phenyl-4-methyl-5-carbethoxy-v-triazole was prepared by the method described in German Pat. No. 2,133,012.

In analogous manner to as described above in Example 4, but employing starting materials, the following compounds of the general formula shown were prepared.

| Example No. | R | Physical Characteristics |
|---|---|---|
| 4a | 4-Cl-C₆H₄- | Yellow, water soluble powder |
| 4b | 3-Cl-C₆H₄- | Yellow, water soluble powder |
| 4c | 4-CH₃O-C₆H₄- | Yellow, water soluble powder |

EXAMPLE 5

18.8 of the triazole described in Example 4 formula:

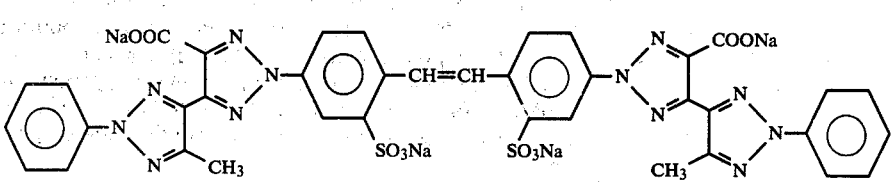

was added to toluene (200 ml) and the mixture heated to 55°. Dimethylformamide (1.0 ml) was added followed by thionyl chloride (2.9 ml) during 15 minutes. The mixture was heated 4 hours at 70°-80° and then absolute ethyl alcohol (50 ml) added. The mixture was refluxed 2 hours and then filtered at 70°, washed with acetone (100 ml) and then water (250 ml). The yellow coloured product was recrystallised from water and dimethylformamide to give the triazole ester of formula:

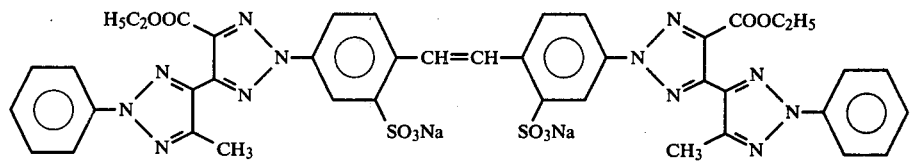

EXAMPLE 6

4:4'-diaminostilbene-2:2'-disulphonic acid (18.5 g) was tetrazotised by the procedure described in Example 1 and the resulting tetrazonium suspension added during 30 minutes to 2-p-chlorophenyl-4-methyl-5-carbethoxy acetyl-v-triazole (32 g) in cellusolve (400 ml) at 32° the pH being kept at 5–6 by addition of anhydrous sodium acetate (10 g). The mixture was heated to 50° during 1 hour, cooled to 20° and the red coloured hydrazone filtered and washed with water (200 ml).

The keto hydrazone was mixed with cellosolve (1000 ml), water (500 ml), ammonium acetate (78.6 g) and cupric chloride dihydrate (36.36 g). The mixture was refluxed for 36 hours and then zinc dust (14 g) and sodium hydrosulphite (10 g) were added. The mixture was filtered to remove insoluble copper compounds and the filtrates cooled to 10°. The yellow coloured precipitate was filtered, washed with water and then recrystallised from a mixture of dimethylformamide (100 ml) and water (100 ml) to give the triazole of formula:

The 2-p-chlorophenyl-4-methyl-5-carbethoxy-v-triazole was prepared in a similar way to 2-phenyl-4-methyl-5-carbethoxy acetyl-v-triazole, the synthesis of which is described in Example 4, above.

In analogous manner to as described above in Example 6, but employing appropriate starting materials, the compounds of the general formula shown were prepared.

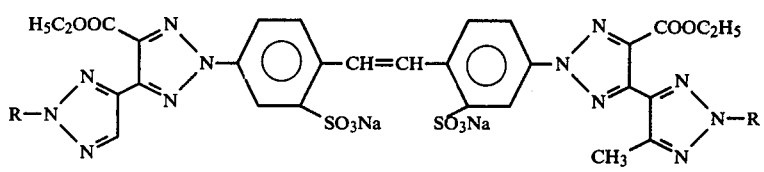

| Example No. | R | Physical Characteristics |
|---|---|---|
| 6a | 3-Cl-C6H4- | Yellow powder |
| 6b | 4-CH3O-C6H4- | Yellow powder |
| 6c | 4-CH3-C6H4- | Yellow powder |

EXAMPLE 7

18.8 g of the triazole described in Example 4 was added to toluene (200 ml) and the mixture heated to 55°. Dimethylformamide (1.0 ml) was added followed by thionyl chloride (2.9 ml) during 15 minutes. The mixture was heated 5 hours at 70° and then cooled to 50°. A steady stream of dry ammonia gas was passed into the reaction during 1 hour at 50°–55°. The mixture was cooled to 10° and the yellow coloured product filtered and recrystallised from a mixture of water and 2-ethoxy ethanol to give the triazole amide of formula

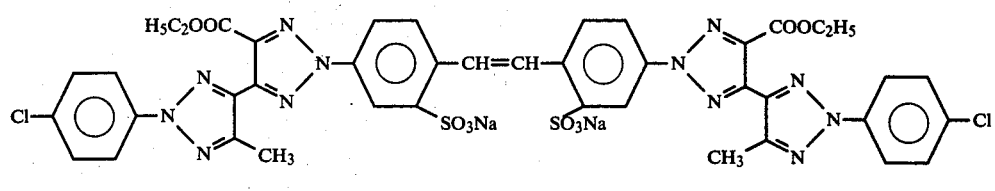

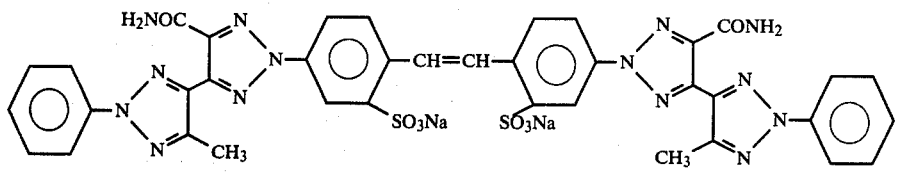

EXAMPLE 8

11.4 g of the triazolyl triazole prepared in Example 1 was dissolved in 52.7 ml concentrated sulphuric acid. The sulphonation mixture was subsequently stirred for nine hours at 100°–110°, then cooled to 40°–50° and stirred into 150 ml cold water. The resultant mixture was neutralised with 30% W/W sodium hydroxide solution and evaporated to dryness. The yellow solid produced was redissolved in water and purified by dialysis through a cellulose acetate membrane. After evaporation of the aqueous solution a greenish yellow powder of formula was obtained.

Following the procedure of Example 8, above, but replacing the compound of Example I, employed therein, by an approximately equivalent amount of the compounds, respectively, of Examples 3, 3e, 3f and 3g, there are obtained, respectively, the compounds of the following table which are of formula

| Example No. | R | Appearance |
|---|---|---|
| 8a | 4-CH₃O-, 3-SO₃Na-phenyl | Yellow solid |
| 8b | 3-NaO₃S-, 5-CH₃-phenyl | Yellow solid |
| 8c | 3-CH₃-, 4-SO₃Na-phenyl | Yellow solid |
| 8d | 3-Cl-, 4-SO₃Na-phenyl | Yellow solid |

EXAMPLE 9

By a similar procedure to that described in Example 8 but by starting with the triazolyl triazole described in Example 4 a compound of the following formula is obtained as a yellow coloured powder

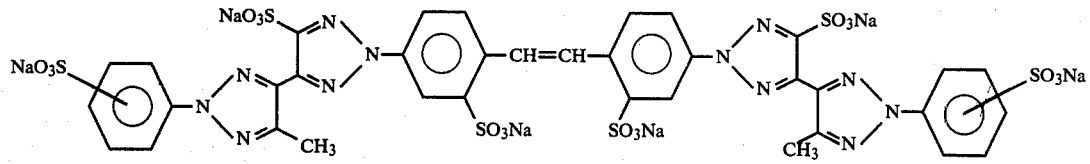

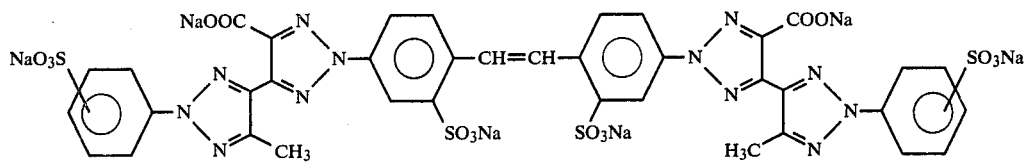

Application Example A

A 5 gram piece of Nylon 6,6 (Banlon) was entered at room temperature into 200 ml of an aqueous solution containing 25 milligrams of the compound described in Example 4 and 150 milligrams of acetic acid. The temperature was raised to 90° over 30 minutes and maintained at 90°–95° for a further 30 minutes, during which time the fabric was agitated mechanically. The fabric was then removed from the liquor, rinsed thoroughly in cold water water, spun dry and dried in an over at 80°. The treated fabric showed a brilliant whiteness compared with the untreated material.

Application Example B

A 5 gram piece of white Nylon 6,6 (Banlon) was treated with 200 ml of a solution containing 25 milligrams of the compound described in Example 4 and 400 milligrams of sodium chlorite. The solution was buffered to pH 3.5. The buffer system consisted of 140 milligrams of sodium perborate, 120 milligrams of sodium nitrate, 120 milligrams of trisodium-polyphosphate and 20 milligrams of a condensation product of di-sec-butylphenol and ethylene oxide, and 2.5 ml of 10% formic acid. The nylon piece was entered into the liquor at 40°. The temperature of the liquor was raised to 90°–95° over 30 minutes and maintained at 90°–95° for a further 30 minutes. The fabric was then rinsed in cold demineralised water, then in a 0.1% aqueous solution of sodium metabisulphite, and again, thoroughly, in cold demineralised water, and finally dried at 80°. The treated piece showed a brilliant neutral hued brightening compared with the untreated material.

Application Example C

A strip of Nylon 6,6 (Banlon) 15 cm wide and weighing 8 gm, was padded at 100% expression through a solution containing 24 milligrams of the triazole described in Example 4. The nylon piece was boiled for 1 minute in 240 ml of water containing 0.2% acetic acid and was then washed off in boiling water for 1 minute. The piece was then rinsed in cold demineralised water and dried in an oven at 80°. The treated fabric showed a brilliant whiteness compared to the untreated Nylon 6,6.

Application Example D

A 5 gram piece of cotton was entered at ambient temperature into 200 milliliters of an aqueous solution containing 25 milligrams of the compound described in Example 4 and 500 milligrams of hydrated sodium sulphate. The cotton was agitated whilst the temperature was raised to 70° over 15 minutes and maintained at 70° for a further 30 minutes, after which it was removed from the bath, rinsed thoroughly in cold water, spun dry and dried in an oven at 80°. The treated fabric showed a brilliant whiteness compared to the untreated cotton.

Application Example E

A strip of cotton, 20 cm wide and weighing 10 g, was padded at 80% expression through a solution containing 0.3% of the compound prepared in Example 8, 7% of Glauber's salt, 7.5% of a carbamide resin pre-condensate, 0.03% of an ethylene oxide condensate of an alkylated phenol, and 1.5% zinc nitrate hexahydrate. The cotton piece was dried at 80° and then kept in an oven at 160° for 5 minutes. The treated fabric was crease-resistant and showed a brilliant whiteness compared to the untreated cotton. Similar results were obtained employing the compound of Example 9, above.

What is claimed is:

1. A compound of formula I″,

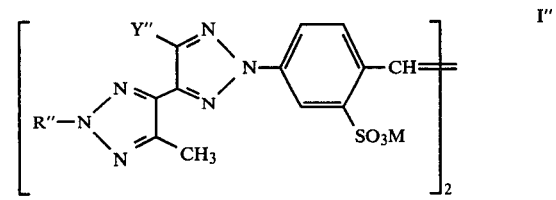

in which Y″ signifies —COOM, —COOR$_1$″, —CONH$_2$, or —SO$_3$M,

R″ signifies phenyl, unsubstituted or mono- or di-substituted by methyl, C$_{1-2}$alkoxy, chlorine, cyano, —CONH$_2$, —COOM, —COOR$_1$″, —SO$_2$CH$_3$, SO$_2$NH$_2$ or —SO$_3$M, R$_1$″ signifies C$_{1-2}$alkyl, and the M's are, independently, hydrogen or a non-chromophoric cation.

2. A compound of claim 1, in which Y″ is other than —CONH$_2$, and in which any phenyl as R″ is unsubstituted or mono-substituted.

3. A compound of claim 1, in which Y″ is —COOM, —COOR$_1$″ or —CONH$_2$, and R″ is phenyl, unsubstituted or mono-substituted by methyl, methoxy, chlorine or —SO$_3$M.

4. A compound of claim 1, wherein Y″ is —SO$_3$M and R″ is phenyl, mono-substituted by —SO$_3$M, or di-substituted, once by —SO$_3$M and once by methyl, methoxy or chlorine.

5. A compound of claim 3, of formula

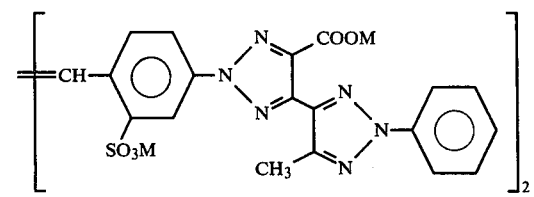

6. A compound of claim 3, of formula

7. A compound of claim 3, of formula

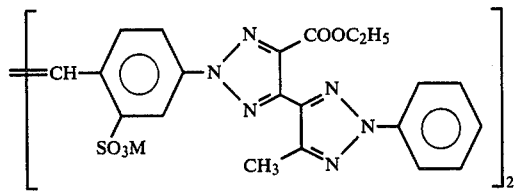

8. A compound of claim 4, of formula

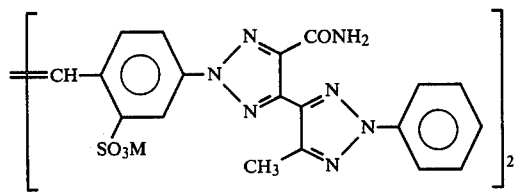

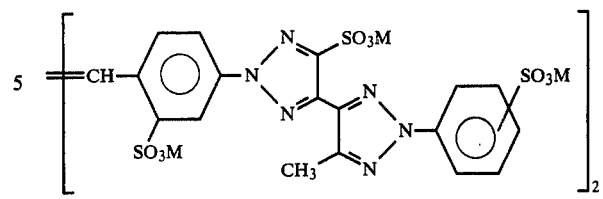

9. A compound according to claim 1 wherein R'', when disubstituted, is substituted once by —SO$_3$M and once by methyl, C$_{1-2}$alkoxy or chlorine.

10. A compound according to claim 1 wherein R'' is unsubstituted phenyl or phenyl monosubstituted by cyano, methoxy, chlorine or —SO$_3$M.

11. A compound according to claim 1 of the formula

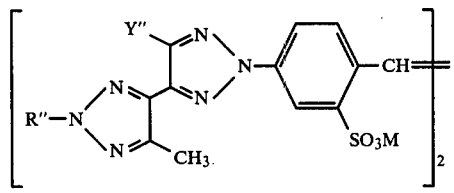

in which Y'' signifies —COOM, —COOR$_1$'' or —CONH$_2$,

R'' signifies phenyl, unsubstituted or mono- or di-substituted by methyl, C$_{1-2}$alkoxy, chlorine, cyano, —CONH$_2$, —COOM, —COOR$_1$'', —SO$_2$CH$_3$, SO$_2$NH$_2$ or —SO$_3$M, R$_1$'' signifies C$_{1-2}$alkyl, and the M's are, independently, hydrogen or a non-chromophoric cation.

* * * * *

UNITED STATES PATENT AND TRADEMARK OFFICE
CERTIFICATE OF CORRECTION

PATENT NO. : 4,167,626
DATED : September 11, 1979
INVENTOR(S) : Fritz Fleck/Alec V. Mercer/Roger Paver It is certified that error appears in the above—identified patent and that said Letters Patent is hereby corrected as shown below:

On the front page, in the left-hand column;

insert --Foreign Application Priority Data

Aug. 14, 1974    United Kingdom    35746/74 --.

Signed and Sealed this

Sixteenth Day of September 1980

[SEAL]

*Attest:*

SIDNEY A. DIAMOND

*Attesting Officer*    *Commissioner of Patents and Trademark*